United States Patent
Delack (10) Patent No.: US 7,645,766 B1
(45) Date of Patent: Jan. 12, 2010

(54) METHOD FOR TREATMENT OF DEPRESSION AND DEPRESSIVE MOOD DISORDERS

(75) Inventor: Elaine A. Delack, Stanwood, WA (US)

(73) Assignee: MedDEV, Inc., Bellingham, WA (US)

( * ) Notice: Subject to any disclaimer, the term of this patent is extended or adjusted under 35 U.S.C. 154(b) by 346 days.

(21) Appl. No.: 11/231,442

(22) Filed: Sep. 20, 2005

Related U.S. Application Data (60) Provisional application No. 60/611,666, filed on Sep. 20, 2004.

(51) Int. Cl.
| | |
|---|---|
| A01N 43/42 | (2006.01) |
| A61K 31/44 | (2006.01) |
| A61K 31/40 | (2006.01) |
| A01N 43/38 | (2006.01) |
| C07D 498/00 | (2006.01) |
| C07D 513/00 | (2006.01) |
| C07D 515/00 | (2006.01) |
| A61K 9/00 | (2006.01) |

(52) U.S. Cl. .................. 514/280; 514/410; 424/400; 546/55

(58) Field of Classification Search ............... 514/280, 514/410; 424/400; 546/55
See application file for complete search history.

(56) References Cited

U.S. PATENT DOCUMENTS 3,961,060 A * 6/1976 Fuxe .................. 514/217

OTHER PUBLICATIONS

Davies Dl et al., 1955, Reserpine in the Treatment of Anxious and Depressed Patients, Lancet 2:115-116.*
Poldinger, 1962, Combined Administration of Desipramine and Reserpine or Tetrabenazine in Depressive Patients, Psychopharmacologia, 4: 308-310 Nurminen et al. 1999, Coffee, cafeine and blood pressure: a critical review, European Journal of Clinical Nutrition, 53: 831-839.*
Haskovec et al., 1967, The Action of Reserpine in Imipramine-Resistant Depressive Patients, Psychopharmacologia, 11: 18-30 Puglia et al. Evaluation of in vitro percutaneous absorption of lorazepam and clonazepam from hydro-alcoholic gel formulations, 2001, International Journal of Pharmaceutics, 228: 79-87.*
Hopkinson et al., 1975, Treatment with Reserpine of Patients Resistant to Tricyclic Antidepressants, Psychiatria. Clin., 8:109-114 Forsman et al., 1983, Reserpine Treatment of Certain Depressive conditions, Current Therap. Research, 34(6):991-998.*
National Institute of Mental Health, Depression, NIH Publication No. 02-3561, 2000.
Mann, et al., Cerebrospinal fluid amines and higher-lethality sucicde attempts in depressed impatients,Biol Psychiatry. Jan. 15, 1997 41(2):162-71.
Youdim, et al., Steroid regulation of monamie oxidase activity in the adrenal medulla, FASEB J Apr. 1989; 3 (6):1753-9.

Ito, M., Long-term depression as a memory process in teh cerebellum, Neurosci Res. Sep. 1986; 3 (6):531-9.
Abraham, et al., Order of onset of substance abuse and depression in a sample of depressed outpatients, Compr Psychiatry. Jan.-Feb. 1999; 40(1):44-50.
Beckmann et al., Serotonin precursors as antidepressive agents: a review, Fortschr Neurol Psychiatr. May 1983;51(5):176-82.
Nolen, et al., L-5HTP in depression resistant to re-uptake inhibitors. An open comparatvie study with tranylcypromine, Br J Psychiatry. Jul. 1985;147:16-22.
Palmer, et al., Electrophysiological effects of monamine-derived aldehydes on singe neurons in neocortex and cerebellum in rats, Alcohol Clin Exp Res. Dec. 1986;10(6):682-5.
Jenkins, et al., Effect of alcohol consumption on hepatic aldehyde dehydrogenase activity in alcoholic patients, Lancet. May 12, 1984;1(8385):1048-9.
Van Alphen, et al., Cerebellar LTD facilitates but is not essential for long-term adaptation of the vestibulo-ocular reflex, Eur J Neurosci. Aug. 2002; 16(3):486-90.
Kornilova, et al., Effect of the character of autonomic response and the emotional and personality . . . , Hum. Physiol. Sep.-Oct. 1999; 25(5) 549-54.
Sakumoto, et al., 5-HT immunoreactive hypothalamic neurons in rat and cat after 5-HTP administration, Brain Res Bull, Jun. 1984; 12(6): 721-33.
Stokes, et al., Biogenic amine and metabolite levels in depressed patients with high versus normal hypothalmic . . . Am J Psychiatry, Jul. 1987; 144(7): 868-72.
Brown, et al., CSF serotonin metabolite (5-HIAA) studies in depression, impulsivity, and violence, J Clin Psychiatry, Apr. 1990; 51 Suppl: 31-41; discussion 42-3.
Van Praag, H.M. Affective disorders and aggression disorders: evidence for a common biological mechanism, Suicide Life Threat Behav. 1986 Summer, 16(2): 103-32.
Rooke, et al. The mitochondrial monoamine oxidase-aldehyde dehydrogenase pathway: a potential site of action of daidzin, J Med Chem, Nov. 2, 2000; 43(22) 4169-79.
Evrard, et al. Altered regulation of the 5-HT system in the brain of MAO-A knock-out mice, Eur J Neurosci. Mar. 2002; 15(5): 841-51.
Egashira, et al. Effects of long-term teratment with dicyclic, tricyclic, tetracyclic, and noncyclic antidepressant . . . Gen Pahrmacol. 12996 Jul; 27(5): 773-8.
Gnerre, et al. Ineraction of psychotropic drugs with monoamine oxidase in rat brain, J Pahrm Pharmacol. Aug. 2001; 53(8): 1125-30.

(Continued)

*Primary Examiner*—Sreeni Padmanabhan
*Assistant Examiner*—Kara R McMillian
(74) *Attorney, Agent, or Firm*—Todd N. Hathaway (57) ABSTRACT

A method for treatment of depression and depressive mood disorders. The patient is administered an amount of a compound that increases the catalytic activity of MAO-A, so as to increase synaptic metabolism of serotonin to 5-HIAL. The effective compound is preferably reserpine, administered in a dosage of less than about 0.03 mg per day. The reserpine may be administered transdermally at a dosage in the range from about 0.002 mg per day to about 0.02 mg per day. A caffeine compound may be administered simultaneously so as to compensate for an antihypertensive effect of the reserpine. The caffeine compound may be combined with the reserpine in a transdermal cream.

6 Claims, 3 Drawing Sheets

OTHER PUBLICATIONS

Lemonde, et al. Impaired repression at a 5-hydroxytryptamine 1A receptor gene polymorphism . . . J Neurosci, Sep. 24, 2003; 23(25): 8788-99.

Larsson, et al. Different effects on the responses of functional pre-and postsynzpitc 5-HT1A receptors by repeated treatment . . . Neuropharmacology, Feb. 1990; 29(2): 86-91.

Chevillard, et al. Estradiol treatment decreases type A and increase type B monoamine oxidase in specific brain stem areas . . . Brain Res Oct. 5, 1981; 222(1):177-81.

Fowler, et al. The effect of age on the activity and molecular properties of human brain monamine oxidase. Neural Transm 1980; 49(1-2): 1-20.

Facts and Comparisons, St. Louis, MO, Reserpine. pp. 1-3.

Youdim, et al. Activation of monoamine oxidase and inhibition of aldehyde dehydrogenase by reserpine, Euro J of Pharm 4 (1968) 105-108.

sigma-aldrich.com/cellsignaling, Major depression.

* cited by examiner

FIG. 1

Serotonin Metabolism in the Nerve Synapse

METHOD FOR TREATMENT OF DEPRESSION AND DEPRESSIVE MOOD DISORDERS

RELATED APPLICATION

This application claims the benefit of U.S. Provisional Patent Application No. 60/611,666 filed on 20 Sep. 2004.

BACKGROUND a. Field of the Invention

The present invention relates generally to the methods for the treatment of depression and other depressive mood disorders, and, more particularly, to methods for treatment of depression and depressive mood disorders by administration of compositions that serve to increase the metabolism and/or turnover of serotonin.

b. Related Art

Major depression is an affective disorder (mood disorder). Common symptoms include: persistent sadness; feelings of hopelessness or pessimism; feelings of guilt, worthlessness, helplessness; loss of interest in hobbies and activities that once gave pleasure; decreased energy; memory deficits and difficulty in making decisions and concentrating; insomnia, early morning wakening, or oversleeping; appetite loss and/or weight loss or overeating and weight gain; suicide ideations or attempts, thoughts of death; physical ailments such as headaches, chronic pain or digestive problems that do not respond to treatment. These symptoms can range from mild to severe, but persist for two weeks or more and often interfere with a person's daily functioning.

According to the National Institute of Mental Health, about 18 million Americans are afflicted with major depression annually. It has been estimated to be the second leading cause of disability, surpassed only by heart disease. Depression is about twice as prevalent in women than men and its occurrence is about two to three times more common in first degree relatives of depressed persons.

Substance abuse such as alcohol is common in persons with depression. It is believed that substance abuse may be a form of self-medication in a person with depression. Alcohol dependence has been shown to follow the onset of depression by an average of 4.7 years, indicating that substance abuse such as the use of alcohol is a pattern of self-medication in depressive disorders (Abraham & Fava (1999). Compr. Psychiatry 40(1): 44-50).

The causes of depression have not been conclusively identified, but it has heretofore generally been believed that depression is a result of inadequate levels of the neurotransmitters, serotonin and norepinephrine, with most emphasis on the former. Prior efforts at treatment of depression have thus concentrated on increasing the levels of serotonin and/or norepinephrine: Past and current antidepressant treatments have consisted of primarily monoamine oxidase inhibitors, tricyclic antidepressants, and serotonin reuptake inhibitors. All of these treatments have been believed to function by increasing the amount of serotonin in nerve synapses (e.g., Sigma-Aldrich, 2003).

The first antidepressant therapies were monoamine oxidase inhibitors (MAO inhibitors) such as iproniazid. Monoamine oxidase has two subtypes, A and B. Monoamine oxidase A (MAO-A) metabolizes both norepinephrine and serotonin. Thus, it has been believed that the antidepressant effect of MAO inhibitors is the result of increased levels of serotonin and norepinephrine due to the MAO inhibitors blocking the breakdown of these neurotransmitters. Despite the proven efficacy of the MAO inhibitors as antidepressants, their use today has become very limited due to the serious side effects associated with MAO inhibitors. One of the side effects is hepatoxicity: MAO is a very important amine-oxidizing enzyme in the liver and the brain, and the inactivation of MAO interferes in the breakdown of tyramine (tyramine is a common amine in food and some beverages). MAO inhibitors can consequently cause excessive amounts of tyramine to accumulate in the brain, which can result in a hypertensive crisis or death. Most of the older MAO inhibitors were irreversible non-selective inhibitors meaning that they inhibited both MAO-A and MAO-B and predominantly inhibited the MAO-B. Today there are several reversible selectively specific MAO-A inhibitors being studied or in use outside of the United States: Because of their reversibility they have a short duration of action, and thus are somewhat less apt to result in the inactivation of liver metabolism and the accumulation of tyramine.

Another class of antidepressant is tricyclic antidepressants, such as imipramine. Tricyclic antidepressants inhibit the reuptake of norepinephrine and serotonin by blocking the reuptake transporters, resulting in increased levels of these neurotransmitters in the nerve synapses (synaptic clefts). Because of the increased levels of the norepinephrine in the nerve synapses excessive cardiac stimulation can result. These cardiac arrhythmias can be difficult to treat and be potentially life threatening. These side effects prompted the development of selective serotonin reuptake inhibitors (SSRIs), which are the most commonly used antidepressants today. Although the SSRIs do not result in increased concentrations of norepinephrine and therefore avoid causing cardiac arrhythmias, the elevation in the serotonin in the nerve synapses can cause agitation, restlessness, gastrointestinal distress and sexual side effects all of which are common symptoms of depression (Sigma-Aldrich, 2003).

The clinical success of SSRIs in treating depression has been interpreted as supporting the prevalent hypothesis that the etiology of depression is a serotonin deficiency. However, it is not clear as to how the SSRIs, tricyclic antidepressants, or MAO inhibitors relieve depression since there is a lag of several weeks before any mood-elevating effects are noticed after these treatments are started, despite the rapid increase in the levels of serotonin in the nerve synapses. Furthermore, the elevated concentrations of the serotonin in the nerve synapses have been shown to cause symptoms common in depression (Sigma-Aldrich, 2003). Also, the administration of serotonin or its precursors was markedly less effective or not effective at all when compared to the MAO inhibitors, tricyclic antidepressants, or the SSRIs in depressed persons (Beckmann and Kasper (1983), Fortschr. Neurol. Psychiatr. 511(5): 176-82; Nolen et al, (1985), Br. J. Psychiatry 147.16-22). So the question arises, if depression is due to the deficiency of serotonin, then why isn't the administration of serotonin or its precursors L-tryptophan or 5-Hydroxytryptophan more or at least equally effective as these antidepressant treatments? And if depression is due to the deficiency of serotonin, then why does it take several weeks before any benefit may be seen from these antidepressant therapies, even though increase the concentration of serotonin in the nerve synapses almost immediately upon administration? As will be described below, the present invention is founded on a new hypothesis that not only resolves these issues but also provides a basis for an improved treatment for depression and other depressive mood disorders.

Accordingly, there exists a need for a method for treatment of depression and other depressive mood disorders, that approaches the root cause of the disorder in a more direct manner than prior art treatments and therefore provides treatment with a greater degree of effectiveness. Furthermore, there exists a need for such a treatment that produces clinical benefits more rapidly than prior art treatments and without a significant lag period between initiation of the treatment and significant mood-elevating results. Still further, there exists a need for such a method that is substantially free of the many negative side effects associated with the prior art treatments. Still further, there exists a need for such a method that is easy to implement and can be made available on a widespread basis to the many sufferers of depression and other depressive mood disorders.

SUMMARY OF THE INVENTION

The present invention has solved the problems cited above, and is a method for treatment of depression and other depressive mood disorders, comprising, broadly, administering to a patient an effective amount of a compound that increases the catalytic activity of MAO-A, so as to increase synaptic metabolism and/or turnover of serotonin. The increased MAO-A activity ensures effective synaptic metabolism of serotonin to the 5-HIAL metabolite that binds to the receptor on the post-synaptic neuron, as opposed to seeking to inhibit metabolism of the serotonin as in prior treatments. The MAO-A agonist may comprise reserpine or a reserpine analogue.

The step of administering the compound for increasing MAO-A activity may comprise administering resperine by transdermal application, preferably at a dosage significantly less than about 0.03 mg/day. The resperine may be administered transdermally at a dosage in the range from about 0.002 mg/day to about 0.02 mg/day; most preferably, it is administered transdermally at a dosage in the range from about 0.006 mg/day to about 0.01 mg/day.

The method may further comprise the step of combining the operative compound with a transdermal cream for the transdermal application. The method may further comprise administering a caffeine compound to the patient so as to compensate for an antihypertensive effect of the preferred reserpine. The reserpine and the caffeine compound may be combined in the transdermal cream, so that they are administered to the patient simultaneously.

The dosage is selected such that the operative compound is administered in an amount that is sufficient to ensure synaptic metabolism of serotonin to 5-HIAL at a level that prevents development of excess concentrations of serotonin in the synaptic cleft, but that is insufficient to deplete serotonin at a rate that results in inadequate release of serotonin into the synaptic cleft.

These and other features are advantages of the present invention will be more fully understood from a reading of the following detailed description with reference to the accompanying drawings.

DETAILED DESCRIPTION

As will be described in greater detail below, the present invention is not postulated on the conventional theory that depression is due to deficient levels of serotonin, but rather on the belief that there is in fact adequate serotonin but insufficient metabolism of the serotonin into the active metabolite 5-Hydroxyindole acetaldehyde (5-HIAL). The present invention consequently employs compounds that act to increase the catalytic activity of MAO-A agonists in order to stimulate synaptic metabolism of serotonin to 5-HIAL. This approach runs contrary to the current antidepressant treatments as discussed above, because a compound that increases MAO-A activity has the effect of decreasing the levels of serotonin in the nerve synapses, whereas the conventional treatments are aimed at increasing serotonin levels.

a. THEORETICAL BASIS

Serotonin is a neurotransmitter. During neurotransmission, serotonin is released from the pre-synaptic neuron into the synapse. It has been heretofore believed that serotonin then travels across the synapse gap and attaches to a specific receptor on the post-synaptic neuron and the nerve transmission is conducted. The present invention is based on an alternative hypothesis, i.e., that it is not the serotonin that activates the post-synaptic receptor, but that instead it is the active metabolite 5-Hydroxyindole acetaldehyde, which is produced within the synapse from the metabolism of serotonin by MAO-A.

Figure 1:
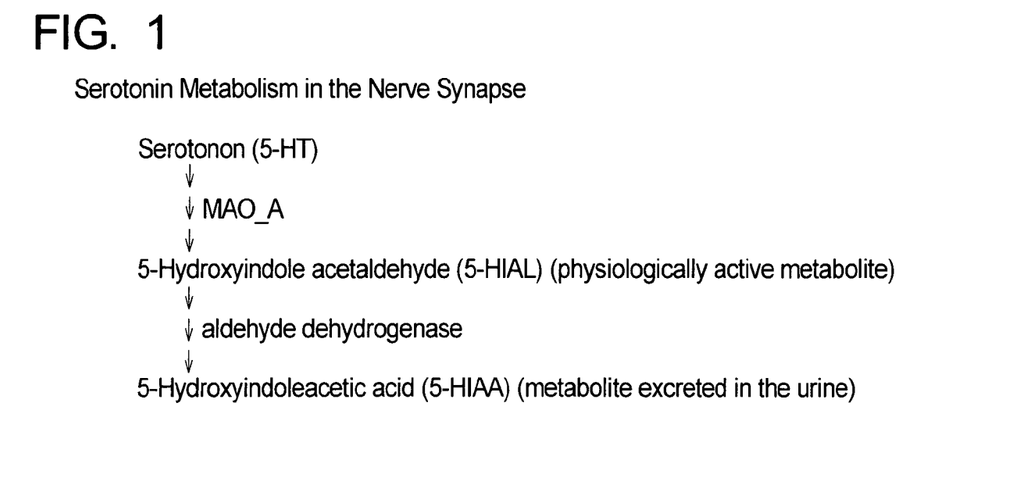
FIG. 1 is a flow diagram showing the phases in serotonin metabolism in the nerve synapse, producing the 5-HIAL active metabolite and the 5-HIAA end metabolite.

As is shown in FIG. 1, serotonin is metabolized by MAO-A into 5-Hydroxyindole acetaldehyde (5-HIAL), which in turn is rapidly metabolized by aldehyde dehydrogenase into 5-Hydroxyindoleacetic acid (5-HIAA), the latter being the major serotonin metabolite that is excreted in the urine. 5-HIAL has been shown to be a physiologically active metabolite, and can activate Long-Term Depression of the cerebellar Purkinje neurons and neurons in the prefrontal cortex (Palmer et al (1986) Alcohol Clin. Exp. Res. 10:682-685). Long-Term Depression of the cerebellar Purkinje neurons and the prefrontal cortex is essential in learning and memory (Ito (1986), Neurosci. Res. 3:531-539). If the cerebellar Long-Term Depression is blocked, the ability to adaptively modify the vestibuloocular reflex is impaired (van Alphen & De Zeeuw (2002), Eur. J. Neurosci 16(3):486-490). Dysregulation of the vestibuloocular system has been correlated with depression, as well as impulsive and autistic personality types (Komilova et al (1999), Hum. Physiol. 25(5):549-54).

The hypothalamus has serotonin accumulating neurons, capacity to uptake 5-Hydroxytryptophan (5-HTP, a precursor of serotonin), with the ability to decarboxylate 5-HTP into serotonin (5-HT), and marked activity of MAO-A to metabolize serotonin into its metabolites 5-HIAL and 5-HIAA (Sakumoto et al (1984), Brain Res. Bull. 12(6)A:721-33). The hypothalamus is involved in cognitive functions; thyroid function; adrenal cortex function that regulates blood pressure, water balance, cortisol production, steroid hormone production; maintenance of the waking state; appetite regulation; sense of well being; body temperature regulation. Many of the symptoms associated with depression can perhaps be correlated to a hypothalamic dysregulation. The activity of the hypothalamic-pituitary-adrenocortical (HPA) axis is often high in depressive disorders. Depressed patients with high HPA activity tend to have impaired MAO-A metabolism of serotonin and norepinephrine resulting in low levels of the active metabolites (Stokes et al (1987), Am. J. Psychiatry 144(7):868-72.

Figure 2:
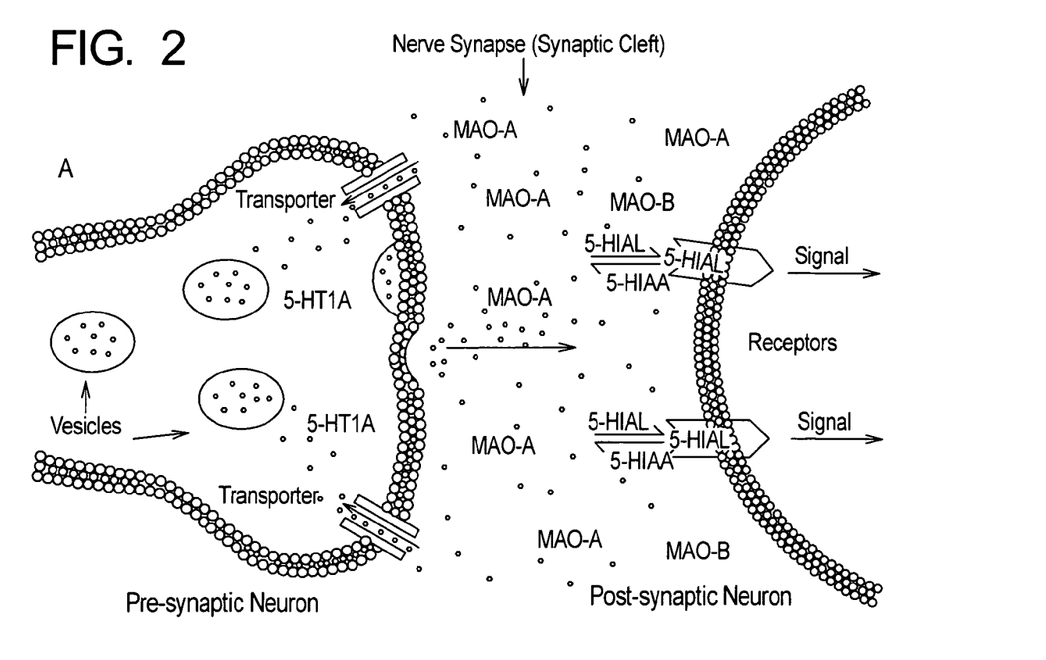
FIG. 2 is a simplified view of a nerve synapse, illustrating the theory on which the treatment of the present invention is based, i.e., that the receptors of the post-synaptic neuron are activated by the 5-HIAL metabolite of serotonin, rather than by the serotonin itself as has been believed in conventional theories.

In view of this evidence, it is believed that the post-synaptic receptor may in fact be activated by the serotonin metabolite 5-HIAL, following the metabolic pathway shown in FIG. 2. Immediately following receptor activation the 5-HIAL is metabolized into 5-HIAA, and which ultimately is excreted in the urine.

By way of verifying this theory, it will be noted that activity of the MAO-A and the 5-HIAL in the serotonin metabolic pathway can be ascertained by measuring the amount of 5-HLAA produced, since the 5-HLAA end metabolite can be easily measured in the cerebral spinal fluid (CSF) or urine of patients. Existing research has shown that the 5-HIAA levels in the CSF of patients with major depression are low, tending to confirm inadequate serotonin metabolism. Furthermore, research by Mann and Malone in 1997 (Biological Psychiatry 41(2):162-171) revealed that the CSF 5-HIAA was significantly lower in depressed patients involved in high-lethality suicide attempts than in the depressed patients having a history of low-lethality suicide attempts. Numerous research studies, conducted in various countries, have yielded similar findings that self-destructive behaviors are associated with low levels of 5-HIAA in the CSF (e.g., Brown & Linnoila (1990), Journal of Clinical Psychology 51: Supplement 31-41; van Praag (1986) Suicide Life Threat Behavior 16(2): 103-132). The prevalent belief, however, has been that the low levels of the serotonin metabolite 5-HIAA observed in depressed patients are due to inadequate levels of serotonin in the nerve synapse; by contrast, in the present invention it is hypothesized that these low levels of 5-HIAA are not due to inadequate levels of serotonin itself, but rather to inadequate metabolism of the serotonin.

The effect of daidzin to suppress ethanol intake in ethanol-preferring laboratory hamsters further supports the instant theory, that deficiency of the 5-HIAL active metabolite is a cause of depression and precipitates substance abuse. Daidzin inhibits aldehyde dehydrogenase, which is the enzyme that metabolizes 5-HIAL to 5-HIAA. Daidzin analogues that inhibit aldehyde dehydrogenase, but not the compound that increases MAO-A activity, have demonstrated a potent antidipsotropic effect, whereas daidzin analogues that potently inhibited the compound that increases MAO-A activity produced no antidipsotropic effect (Rooke et al (2000), Lancet Journal 1(8385):1048-1049). Furthermore, it has been shown that alcohol consumption inhibits aldehyde dehydrogenase, resulting in increased concentrations of 5-HIAL (Jenkins et al (1984), Lancet 1(8385): 1048-1049). This would appear to explain the pattern of self-medication via alcohol abuse that is commonly observed in patients having depressive disorders.

Research has also shown that a genetic deficiency of the compound that increases MAO-A activity induces major alterations in mood and behavior in animals and humans. Knockout mice lacking the compound that increases MAO-A activity were found to have high levels of extracellular serotonin and, conversely, 40% lower spontaneous firing of the serotonergic neurons in the dorsal raphe nucleus (Evrard et al (2002), Eur. J. of Neurosci. 15(5):841-851). The dorsal raphe nucleus is a major area of the brain affected in depressive disorders. This research supports the present hypothesis that serotonin is not the activator of the receptor on the post-synaptic serotonergic neuron, but rather that the serotonin metabolite 5-HIAL is the activator of the post-synaptic receptor, resulting in the firing of the serotonergic neurons such as in the dorsal raphe nucleus.

Accordingly, referring again to FIG. 2, the theory on which the present invention is founded may be stated as follows: During neurotransmission, serotonin is released into the synaptic cleft from storage vesicles present in the pre-synaptic neuron. The serotonin is then metabolized in the synaptic cleft by MAO-A, into the active metabolite 5-HIAL. The 5-HIAL binds to the receptor on the post-synaptic neuron, thereby transferring the signal. The 5-HIAL is then rapidly metabolized by aldehyde dehydrogenase into 5-HIAA, which is eventually excreted in the urine.

Assuming this is correct, then depression and other mood disorders may properly be attributed to reduced availability of the 5-HIAL metabolite rather than to low levels of serotonin, as has been previously assumed. The present invention therefore addresses the reduced availability of 5-HIAL by administering to the patient a compound (referred to from time-to-time as an MAO-A agonist) that increases the catalytic activity of MAO-A, thereby increasing metabolism of the serotonin to 5-HIAL. The operative compound (MAO-Agonist) is suitably reserpine or a reserpine analogue.

The dose of the reserpine or other operative compound should be sufficient to metabolize the serotonin to 5-HIAL at a rate that prevents elevated concentration of non-metabolized serotonin from developing in the synaptic cleft, as this would result in too much serotonin being bound to the transporter, and would in turn result in the increased activation of 5-HT1A and therefore decreased release of serotonin and inhibition of MAO-A. Yet the dose should not be so high that the synthesis of serotonin is unable to keep up with the turnover rate, as this would deplete the stores of serotonin in the storage vesicles and result in inadequate release of serotonin into the synaptic clef, which in turn would result in inadequate 5-HIAL production and therefore inadequate activation of the post-synaptic neuron. Administering too high of dose of the operative compound consequently results in an undesirable increase in the symptoms of depression, as has in fact been observed, with excessive dosages of reserpine; however, it has been found that these symptoms are rapidly resolved upon decreasing the dosage to levels suitable for the individual patient.

b. COMPARISON WITH MAO-A INHIBITORS AND SSRIS

The observed efficacy of the present invention appears to confirm that inducing an increase in the metabolism of serotonin to 5-HIAL has a strongly beneficial effect in treating mood disorders, and has a profoundly more immediate impact than the current antidepressant therapies of MAO inhibitors, tricyclic antidepressants, and serotonin reuptake inhibitors. Furthermore, as noted above, intentionally increasing metabolism of serotonin runs directly contrary to the conventional belief regarding the etiology of depression. Yet, it is incontestable that MAO inhibitors, tricyclic antidepressants, and serotonin reuptake inhibitors also produce significant benefits when treating depression. This apparent contradiction may be explained as follows, making reference to FIGS. 3A-3B and 4A-4B:

Research has shown that MAO inhibitors as well as tricyclic antidepressants (imipramine, clomipramine, amitriptyline, zimeldine, viloxazine, nortriptyline, maprotiline, nomifensine, and doxepine) and some serotonin reuptake inhibitors (fluoxetine, fluvoxamine, citalopram)) demonstrate inhibitory activity towards both MAO-A and MAO-B, but with clearly more potent selectivity for MAO-B. Long-term administration (four weeks or more) of these antidepressants consequently results in a significant increase in the inhibition of MAO-B relative to inhibition of MAO-A. Furthermore, these antidepressants are competitive inhibitors of MAO-A but noncompetitive inhibitors of MAO-B (Egashira et al (1996), Gen. Pharmacology 27(5):773-778; Gnerre et al (2001), J. of Pharm & Pharm. 53(8):1125-1130). Competitive inhibitors have a more reversible effect, in that saturating concentrations of the substrate (such as increased levels of the substrate serotonin or norepinephrine) can remove the inhibition, thus negating the MAO inhibitory effect. Noncompetitive inhibitors, however, are irreversible and do not compete with the natural substrate, so that an increased concentration of the substrate (i.e., serotonin or norepinephrine) does not negate the MAO inhibitory effects.

Figure 3A:
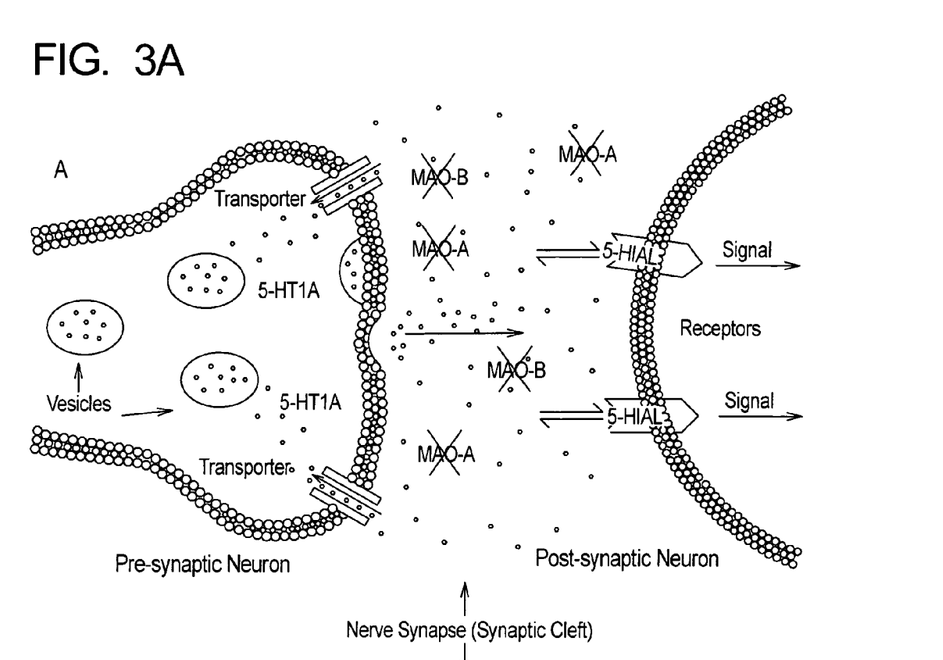
FIGS. 3A-3B are simplified views of a nerve synapse, similar to FIG. 2, illustrating the mechanism of conventional MAO inhibitors, as hypothesized by the inventor herein pursuant to the theory on which the present invention is based.

Consequently, as can be seen in FIG. 3A, MAO-A Inhibitors initially inhibit both MAO-A and MAO-B, the inhibition of MAO-A being competitive and that of the MAO-B being noncompetitive as described above. Inhibition of the MAO-A inhibits metabolism of serotonin to 5-HIAL, so that continued release of serotonin from the vesicles of the pre-synaptic neuron results in an increased concentration of serotonin in the synaptic cleft. As can be seen in FIG. 4B, the increased serotonin levels in turn compete with the MAO-A Inhibitor, resulting in a negation of the MAO-A inhibition.

Figure 3B:
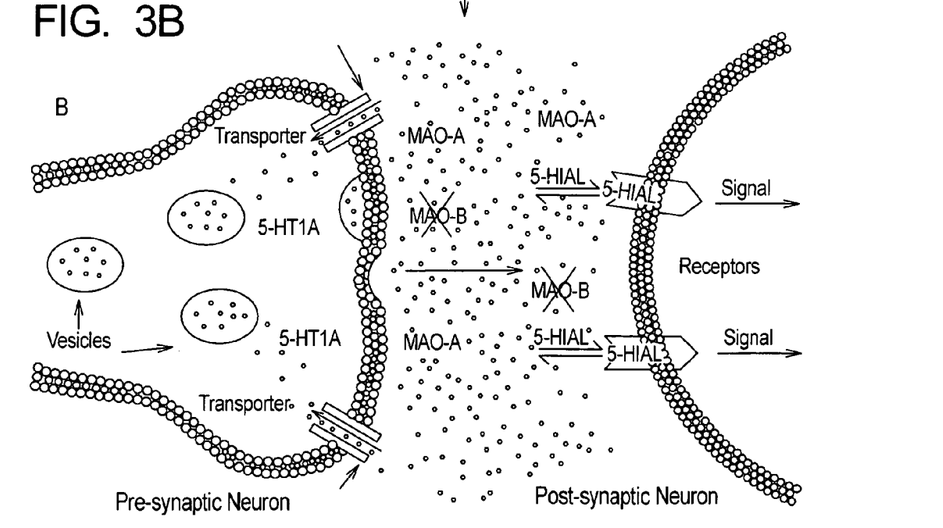

Thus, it is believed that the conventional antidepressants noted above have only a short-acting MAO-A inhibitory effect, because after a few weeks of treatment the concentration of the substrates (serotonin or norepinephrine) increase to the level capable of negating the MAO-A inhibitory effect, while the MAO-B inhibitory effect persists indefinitely. The ultimate result is an increased ratio of MAO-A:MAO-B activity, with the MAO-A being proportionally higher. The increased MAO-A levels, in turn, cause increased metabolism of the serotonin to the metabolite (5-HIAL) that activates the receptors of the post synaptic neurons. This would appear to account for the antidepressant effect of conventional treatments, and may also explain why there is a lag of several weeks before any benefit is seen when using prior antidepressants.

Figure 4A:
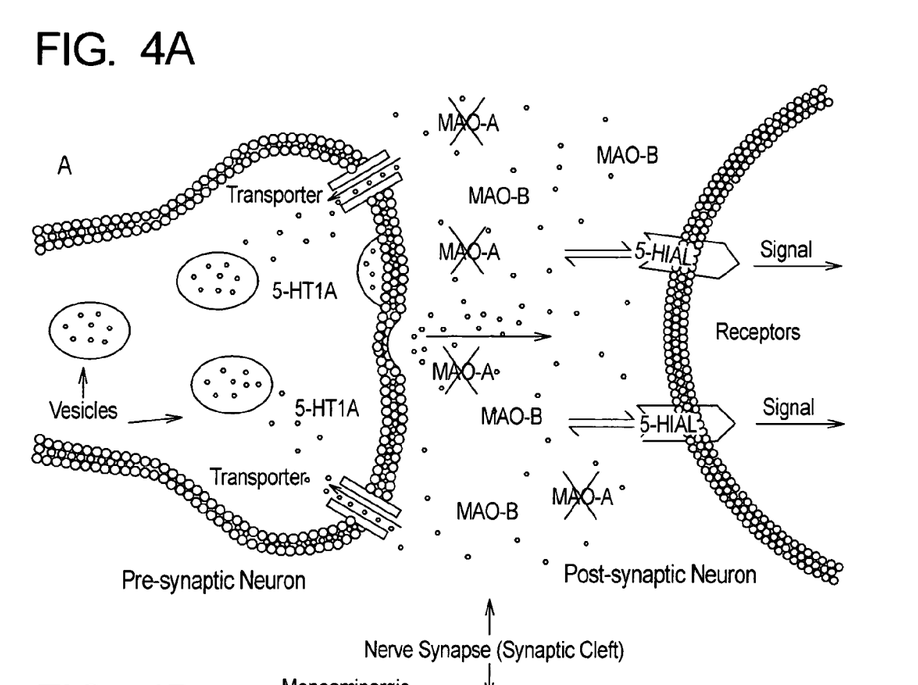
FIGS. 4A-4B are simplified views of a nerve synapse, similar to FIGS. 3A-3B, illustrating the mechanism of conventional selective serotonin reuptake inhibitors (SSRIs), as hypothesized by the inventor herein pursuant to the theory on which the present invention is based.
Figure 4B:
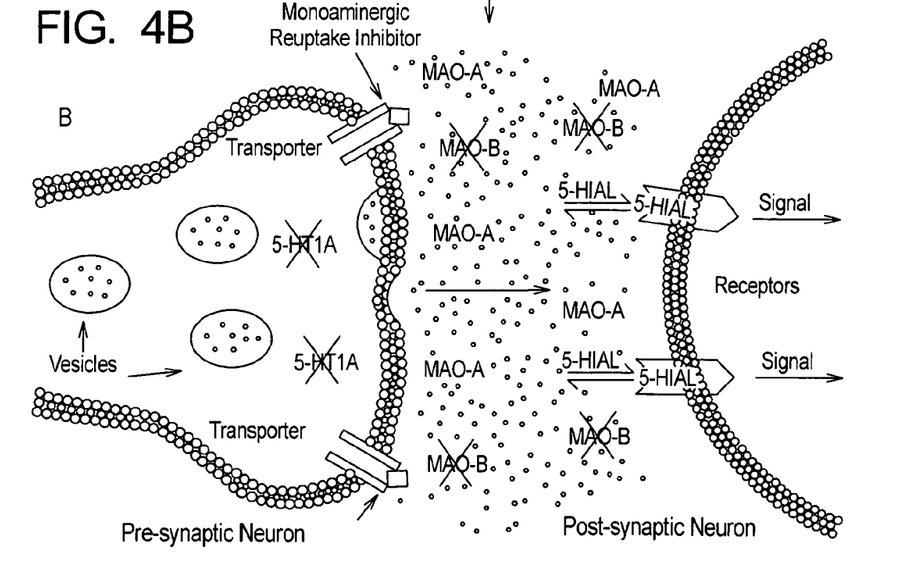

As is shown in FIGS. 4A-4B, the benefits observed with SSRIs and tricyclic antidepressants may in turn be due to the effect of reducing inhibition of the release of serotonin from the pre-synaptic nerve. Inhibition of serotonergic neurons is mediated by 5-HT1A autoreceptors. Serotonin that is not metabolized in the nerve synapse binds to the serotonin transporter, which reuptakes the serotonin from the nerve synapse and carries it back into the presynaptic serotonergic neuron. This serotonin that is taken back up into the presynaptic neuron activates the 5-HT1A autoreceptors in the presynaptic neuron, resulting in a decrease in the release of serotonin into the nerve synapse. The activation of the 5-HT1A autoreceptors, by the reuptake of the serotonin, also induces inhibition of the MAO-A activity, resulting in a decrease in the synapse metabolism of serotonin to the active metabolite 5-HIAL (Larsson et al, 1990).

As shown in FIG. 4B, SSRIs and tricyclic antidepressants block the binding of the serotonin to the serotonin transporter, which in turn prevents the activation of the 5-HT1A autoreceptor. As a result, serotonin continues to be released into the synaptic cleft, from the storage vesicles in the pre-synaptic neuron, despite already elevated levels in the cleft. Furthermore, the metabolism of serotonin into the active 5-HIAL metabolite is inhibited by the SSRIs by competitive inhibition of MAO-A, similar to the effect of the MAO-A inhibitors described above.

The net result is a significant increase in the concentration of serotonin in the synaptic cleft. After a period of delay, the elevated serotonin concentrations induce additional MAO expression, and furthermore the increased concentration of serotonin results in a negation of the MAO-A inhibitory effect of the SSRI. SSRIs (like the MAO inhibitors) are also noncompetitive inhibitors of MAO-B, so that irreversible inhibition of MAO-B also results in an increased ratio of MAO-A: MAO-B activity. These effects become more pronounced the longer the therapy is administered, finally resulting in increased 5-HIAL levels. This would appear to explain the beneficial effects of SSRIs, and why there is again usually a lag of several weeks before such effects are seen.

5-HT1A autoreceptors have been shown to be genetically expressed twofold higher in depressed patients and fourfold higher in completed suicide cases (Lemonde et al (2003), J. of Neurosci. 23(25):8788-8799). Consistent with the above explanations, the known genetic link to expression of the 5-HT1A autoreceptors, coupled with the fact that high levels of estrogen will inhibit MAO-A activity (Youdim et al (1989), FASEB Journ. 4(6):1753-1759; Chevillard et al (1981) Brain Res. 222(1):177-181), may explain the genetic and gender prevalence of depressive disorders. Research has also shown that the ratio of MAO-A:MAO-B activity decreases with age (Fowler et al (1980), J. of Neur. Trans. 49(1-2):1-20), which may explain the prevalence of depression in the elderly.

c. METHOD OF PRESENT INVENTION

The present invention provides a method for treatment of depression and other mood disorders, by the application or administration of a compound (which may be referred to for purposes hereof as an MAO-A agonist) that increases the catalytic activity of MAO-A in metabolizing serotonin to its active metabolite 5-HIAL. Suitable compounds includes reserpine and reserpine analogues; as used herein, the term "reserpine analogue" refers to compounds having a pharmacological effect similar to reserpine, in effecting an increase in the catalytic activity of MAO-A. Reserpine in particular has been shown to activate MAO-A, as well as to inhibit aldehyde dehydrogenase (Youdim & Sandler (1968) Eur. J. of Pharm. 4:105-108). It is anticipated that other rauwolfia alkaloids and their analogues may also be useful.

The treatment composition of the present invention may be administered by any suitable means, such as orally, or by transdermal application, or injection, or inhaler, to give just a few examples. However, administration by transdermal application is generally preferred, in that this provides significant advantages in terms of ease of use and more consistent dosage levels.

Accordingly, a preferred composition for use in the treatment of the present invention is formed by the preferred MAO-A agonist reserpine in a transdermal cream. When transdermally administered, daily dosage is significantly less than 0.03 mg/day and preferably within the range of about 0.002-0.02 mg/day, with a range of about 0.006-0.01 mg/day being most preferred. The treatment composition is suitably applied in a single daily dose, e.g., 0.01 mg of the MAO-A agonist in 0.05 ml of transdermal cream applied once every morning. Caffeine may also be included in the composition to compensate for the anti-hypertensive effect of the preferred reserpine; the caffeine may suitably be included in an amount from about 50-100 mg/dose.

As has been explained above, the present invention differs profoundly from previous methods used for treatment of depression. Based on the prior theories and antidepressant treatments, administration of any agent that would enhance the metabolism of serotonin would be strongly contraindicated. Current conventional antidepressant medications are aimed at increasing the levels of serotonin: The MAO inhibitors are aimed at preventing, rather than increasing, metabolism of serotonin, which the tricyclic antidepressants and serotonin reuptake inhibitors are similarly aimed at maintaining higher levels of serotonin in the nerve synapses. The use of a MAO-A agonist therefore runs directly contrary to the purpose of both types of treatment, and even more so against the recent trend toward the use of specific MAO-A inhibitors as a treatment for depression. In point of fact, the drug information reference "Facts and Comparisons 2002" states expressly that reserpine is contraindicated in mental depression, or where there is a history of mental depression, especially with suicidal tendencies.

d. EXAMPLES

The following illustrative examples relate to actual practice of the invention described above, and its success in alleviating the symptoms of depression and facilitating the cessation of substance abuse.

Example One

A 44-year old, 250-pound male suffering from depression was treated in accordance with the method of the present invention. The patient reported suffering from the following persistent symptoms of depression for four years prior to treatment.
  Persistent anxious mood
  Feelings of hopelessness, pessimism
  Feelings of guilt, worthlessness
  Loss of interest or pleasure in hobbies and activities that were once enjoyed
  Decreased energy, fatigue
  Difficulty concentrating, remembering, making decisions
  Insomnia, early-morning awakening, daytime sleeping
  Overeating and weight gain
  Thoughts of death or suicide
  Persistent physical symptoms that do not respond to treatment—headaches and gastric upset
  Inability to stop drinking until inebriated if offered alcohol Treatment was in the form of 0.01 mg of reserpine per 0.05 ml of transdermal cream, applied transdermally once a day in the morning. Within four hours of the first application of the treatment, the patient reported a significant improvement in his state of mind, and that the negative outlook and emotions identified above had resolved. The patient has continued on the treatment, and remains free of all of the prior symptoms so long as the consecutive 24-hour dosing regimen is followed. Moreover, he has ceased overeating and has lost in excess of 20 pounds during the treatment. In instances where the patient has forgotten to take the dose for a day, symptoms have begun to return within about 32 hours of the last dose administered (reserpine has a 33 hour therapeutic half-life in the human body). When the dose was missed for 72 hours, the patient displayed agitation, difficulty concentrating, feelings of worthlessness and pessimism; however, within one hour of applying the missed dose, the patient was free of all symptoms. The patient has had an occasional beer or mixed drink while socializing with friends during the treatment, but often has not even finished the drink.

Example Two

A 44-year old, 175-pound female suffering from depression was treated in accordance with the method of the present invention. The patient reported suffering from the following persistent symptoms of depression for 15 years prior to treatment:
  Persistent sad mood with frequent episodes of weeping for no reason
  Feelings of hopelessness and pessimism
  Feelings of helplessness
  Decreased energy, fatigue
  Difficulty concentrating, remembering, making decisions
  Insomnia
  Overeating and weight gain
  Persistent physical symptoms that do not respond to treatment—headaches, acne, and hair loss.

The treatment consisted of 0.01 mg of reserpine per 0.05 ml of cream, applied transdermally by rubbing the cream into the skin once a day in the morning. Within one hour of applying the dose the patient reported increased energy; she developed a headache and some nausea that persisted for the first eight hours after initiation of the treatment, but then spontaneously resolved. Within 10 hours of the first application the patient reported all perceptible symptoms had resolved, with the exception that she still had some slight problems with memory. The patient continued on the treatment for 30 consecutive days with no return of her symptoms during that time. The patient averaged weight loss of one to two pounds per week during the 30-day course of treatment. The treatment was interrupted for 10 days at the end of the first 30 consecutive-day treatment; all of the symptoms returned during this period of abstinence from the treatment, and the weight loss halted despite no marked change in her diet. The patient then resumed the treatment, and within one hour of doing so she reported that her symptoms had again resolved. She also resumed the 1-2 pound per week weight loss. She lost a total of 15 pounds during the first 50 days, and continues on treatment.

Example Three

A 20-year old, 220-pound male suffering from depression and substance abuse (marijuana use twice a day, and consumption of alcohol to the point of inebriation about twice a week) had tried unsuccessfully to stop the substance abuse several times in the preceding three years. The longest period he was able to abstain from smoking marijuana was two weeks, due to "intense cravings". The patient reported suffering from the following persistent symptoms of depression for 5 years prior to treatment:
  Persistent sad and "empty" mood
  Feelings of pessimism
  Decreased energy
  Insomnia
  Overeating and weight gain
  Thoughts of death but not suicide
  Persistent physical symptoms that do not respond to treatment—headaches and stomach cramps The treatment consisted of 0.01 mg of the reserpine per 0.05 ml of cream, applied transdermally by rubbing the cream into the skin once a day in the morning. Within two hours of applying the first dose all of the pessimism and negative mood aspects listed above resolved, and he also reported experiencing no cravings for marijuana or alcohol. On the third day of treatment, the patient reported some feelings of sadness and decreased energy; the dose was then decreased to 0.0075 mg of reserpine, and the symptoms resolved that same day. He has not used any marijuana during the treatment and he reports having no cravings for the substance. He does have an occasional single beer, about twice a month, but he reports no desire to drink alcohol. He lost five pounds during the first 60 days and continues on the treatment.

Example Four

A 64-year old female with a family history of depression and a personal history of major clinical depression, who had been hospitalized in 1975 and again in 1990 with major episodes of depression, including extreme suicidal ideations. Numerous different medications were tried in an effort to stabilize her condition, with only limited success. Since 1990 she had been taking 25 mg to 75 mg of nortriptyline to manage her depression, and reported having to increase the dose to as high as 100 mg during stressful life events. The patient experienced dry mouth and constipation as side effects of using nortriptyline. The patient reported suffering from the following symptoms, despite taking nortriptyline:

Decreased energy, fatigue

Early morning awakening

The patient discontinued the use of nortriptyline and the same day started the treatment of the present invention, using 0.01 mg of the reserpine per 0.05 ml cream, applied transdermally by rubbing the cream into the skin once a day in the morning. Within one hour of applying the first dose the fatigue and loss of energy resolved. She reported increased energy throughout the day and she did not experience tiredness in the evening as per usual on the nortriptyline. Early in the treatment she reported that she was going through a very stressful time in her life, that in the past would have required her to increase her dose of nortriptyline as high as 100 mg in order to cope with the stress, but she has not had to increase the dosage when using the treatment of the present invention. After 10 months of consecutive daily treatment using 0.01 mg of the MAO-A activity stimulator (reserpine) per 0.05 ml cream applied transdermally, with no return of the symptoms listed above, the patient experienced some insomnia and fatigue during a prolonged, very stressful event (a lawsuit). The patient increased the dose to 0.02 mg of the MAO-A activity stimulator for one week, and insomnia and fatigue resolved. After the stressful event was completed, the patient returned to the 0.01 mg dose of the MAO-A activity stimulator, with no return of any symptoms of depression.

Example Five

A 24-year old female weighing 180 pounds with a clinical diagnosis of depression. This patient had been using a serotonin reuptake inhibitor (SSRI) for three months with moderate effect in alleviating her symptoms of depression, with the exception of labile emotions consisting of transient irritability. The patient experienced a 15-pound weight gain while using the serotonin reuptake inhibitor.

Due to the weight gain, the patient had discontinued the use of the serotonin reuptake inhibitor for a period of two months prior to starting the treatment of the present invention. She reported that during this lapse in treatment all of her symptoms of depression had returned, which included:

Insomnia

Fatigue throughout the day

Labile emotions including irritability and spontaneous crying

Feelings of hopelessness and "doom and gloom"

The patient then started the treatment of the present invention, using 0.01 mg of the MAO-A activity stimulator (reserpine) per 0.05 ml cream, applied transdermally by rubbing the cream into the skin once a day in the morning. The patient experienced a headache that did not resolve spontaneously the first day, so the dose was reduced to 0.002 mg the second day. The headache resolved immediately with the lower dose of 0.002 mg and the patient reported alleviation of her symptoms of feeling hopelessness and "doom and gloom", but her other symptoms persisted. On the third day the dose was therefore increased to 0.004 mg of the MAO-A activity stimulator; in response, she reported improvement in her emotions stating, "I don't cry at the drop of a hat". At the 0.004 mg dose (reserpine) level her feeling of hopelessness was alleviated, and she was more emotionally stable as well, but she still experienced fatigue and insomnia. The does was consequently increased to 0.006 mg per day, at which point all of the patient's symptoms of depression were successfully alleviated. She has been on the treatment for eight consecutive months, using 0.006 mg per day of the reserpine applied transdermally, with no return of the symptoms of depression listed above.

It will be noted that in each of the examples the improvement or resolution of symptoms was essentially immediate, occurring within 1-4 hours of the first application of the treatment composition. This stands in dramatic contrast to the delay of 2-3 weeks characteristic of conventional treatments. Moreover, in all examples, the treatment has proceeded with no significant negative side effects; the preferred reserpine (and other rauwolfia alkaloids) have known negative side effects at higher dosage rates, however, the dosage rates used in the method of the present invention are well below those ranges. Moreover, the preferred MAO-A activity stimulator—reserpine—is comparatively economical, so that the invention can be practiced without prohibitive expense.

It is to be recognized that various alterations, modifications, and/or additions may be introduced into the construction and arrangements of parts described above without departing from the spirit or ambit of the present invention as defined by the appended claims.

What is claimed is:

1. A method for treatment of depression and depressive mood disorders, comprising:

administering to a patient in need thereof an effective amount of a compound that increases the catalytic activity of MAO-A, so as to increase synaptic metabolism of serotonin to 5-HIAL, the step of administering to a patient an effective amount of a compound that increases the catalytic activity of MAO-A comprising:

administering reserpine as the sole active ingredient by transdermal application at a dosage of 0.002 mg/day to about 0.02 mg/day.

2. The method of claim 1, wherein the step of administering said reserpine by transdermal application comprises:

administering reserpine transdermally at a dosage in the range from about 0.006 mg/day to about 0.01 mg/day.

3. The method of claim 1 further comprising the step of:

combining said reserpine with a transdermal cream for said transdermal application.

4. A method for treatment of depression, and other depressive mood disorders, comprising:

administering reserpine as the sole active ingredient, to a patient in need thereof transdermally, at a dosage of about 0.002 mg/day to about 0.02 mg/day.

5. The method of claim 4, wherein the step of administering said reserpine transdermally comprises:

administering said reserpine in a transdermal cream at a dosage in the range from about 0.002 mg/day to about 0.02 mg/day.

6. The method of claim 4, wherein the steps of administering said reserpine transdermally comprises:

administering said reserpine in a transdermal cream at a dosage in the range from about 0.006 mg/day to about 0.01 mg/day.

* * * * *